United States Patent [19]

Speiser et al.

[11] Patent Number: 4,810,697

[45] Date of Patent: Mar. 7, 1989

[54] PHARMACEUTICAL FORMULA

[76] Inventors: Peter Speiser, Freudenbergstr. 101, CH-8044 Zürich; M. Orhan Vaizoglu, Kinkelstr. 28, CH-8006 Zürich, both of Switzerland

[21] Appl. No.: 434,572

[22] Filed: Oct. 15, 1982

[30] Foreign Application Priority Data

Oct. 16, 1981 [CH] Switzerland ............... 6627/81
Jan. 19, 1982 [CH] Switzerland ............... 314/82

[51] Int. Cl.$^4$ ............... A61K 31/685; A61K 31/66; A61K 31/22; A61K 31/225
[52] U.S. Cl. ............... 514/77; 514/112; 514/114; 514/76; 514/519; 514/546; 514/547; 514/548; 514/549; 560/193; 560/198; 560/199
[58] Field of Search ............... 424/312; 560/193, 198, 560/199; 514/77, 112, 114, 76, 519, 546, 547, 548, 549

[56] References Cited

U.S. PATENT DOCUMENTS 4,440,777  4/1984  Zupan ............... 424/45

Primary Examiner—Frederick E. Waddell

Attorney, Agent, or Firm—Foley & Lardner, Schwartz, Jeffery, Schwaab, Mack, Blumenthal & Evans

[57] ABSTRACT

The present invention concerns a pharmacological vehicle or carrier system, which makes possible administration of the active ingredient with a high absorption thereof in the blood circulation of the patient treated therewith, in particular also in the case of oral administration. The pharmacological vehicle system according to the invention comprises ultrafine particles of a reaction product of a reactive derivative of an at least dibasic inorganic acid or an alkane-carboxylic acid having 2 or 3 carboxyl groups and optionally one or two hydroxy groups, wherein one bond of the dibasic inorganic acid or one carboxy group of the alkane-carboxylic acid is bonded to a pharmacological active ingredient containing a hydroxy group, SH group and/or a primary or secondary amino group having a ractive hydrogen atom on this group, and the other bond is bonded to the free hydroxy group of a glycerolipid having at least one free hydroxy group on the glycerol. The invention further concerns these reaction products and a process for the preparation of ultrafine particles of these reaction products.

13 Claims, No Drawings

PHARMACEUTICAL FORMULA

The present invention concerns a pharmaceutical vehicle or carrier system which makes possible administration of the active ingredient with high absorption thereof into the blood of the patients treated therewith, particularly also in the case of oral administration. The pharmaceutical vehicle system of the invention comprises ultrafine particles of a conversion product of a reactive derivative of an at least dibasic inorganic acid or an alkanecarboxylic acid having 2 or 3 carboxyl groups and possibly one or two hydroxy groups, wherein one bond of the dibasic inorganic acid or one carboxy group of the alkane-carboxylic acid is bonded to a pharmacological active ingredient which has a hydroxy group, an SH group and/or a primary or secondary amino group having a reactive hydrogen atom on said group, and the other bond is bonded to the free hydroxy group of a glycerolipid having at least one free hydroxy group on the glycerin. The invention further concerns these conversion products themselves, as well as processes for the preparation of the ultrafine particles themselves.

In the case of many pharmaceutical preparations, effectiveness is restricted, in particular because, as the result of the hydrophilic nature of their molecules, the active ingredients are able to pass only slightly or not at all through the boundary layer of organs during their retention thereon, e.g., the mucosa of the gastro-intestinal tract during passage therethrough, in the case of oral administration. Numerous active ingredients contain in their molecule either hydroxy, SH and/or primary or secondary amino groups, the hydrogen atoms of which are reactive. In the pharmaceutical vehicle systems according to the invention, active ingredients containing a hydroxy group, a SH group and/or primary or secondary amino groups are bonded by means of a physiologically readily cleavable bridge element having two reactive centers, to the hydroxy group of a glycerolipid having at least one free hydroxy group, while the other hydroxy groups are saturated partially or entirely by substituents which lend the complete molecule a lipophilic character, thereby improving its passage through membranes or boundary layers. By varying the substituents on the other hydroxy groups of the glycerolipid depending on the lipophilic nature of the active ingredient, the lipophilia of the entire molecule may be controlled and thus much better adjusted for optimum passage through the membrane of the organ targeted. The use of the selected bridge element between the glycerolipid and the active ingredient assures the ready release of the active ingredient following its passage through the boundary layer, without producing molecular fragments of the bridge having undesirable physiological properties or effects of their own as a result of the clevage. By virtue of their lipophilic-amphiphilic properties, the compounds according to the invention may be converted with water or an isotonic salt solution into ultrafine, disperse suspensions, i.e., suspensions of particles having a particle size in the nanometer range (less than 1 $\mu$m or $10^{-3}$ mm), so that further auxiliary substances, except water, are no longer required. The stability of the pharmaceutical preparations prepared in this manner and that of the prodrugs formed by the covalent bonding of individual components is assured over a surprisingly long period of time. As a result of the fact that no further auxiliary substances are incorporated and the active ingredients are bound to only physiological lipids, only the toxicity of the of the active ingredients plays a role.

The subject matter of the invention thus is a pharmaceutical vehicle or carrier system comprising ultrafine particles of a compound having the general formula

wherein A is the residue obtained after the reaction of the reactive hydrogen of the active ingredient which contains one or more hydroxy groups, SH groups and/or primary or secondary amino groups having reactive hydrogen atoms, R is the bridge element having two reactive centers, and L is the residue obtained after the reaction of the free hydroxy group of a glycerolipid containing at least one free hydroxy group. Also the subject matter of the present invention are the prodrugs of the formula

themselves. If the active ingredient A—H contains several hydroxy groups, SH groups and/or primary or secondary amino groups with a reactive hydrogen atom, several —R—L vehicle residues may be combined with the active ingredient, e.g., in order to obtain the desired lipophilia of the complete molecule, by using suitable amounts of the reactive components forming the bridge element R and of the glycerolipids with at least one free hydroxy group.

Particularly suitable bridge elements are $SO_2$—, —PO(OH)—, —CO—, the residues of alkanedicarboxylic acids, alkane-tricarboxylic acids, alkane-mono- or dihydroxydicarboxylic acids and alkane-mono or dihydroxytricarboxylic acids, wherein the alkane radical may contain 1 to 6 carbon atoms. These residues which yield bridge elements are, for example, sulfurylchloride, phosphoric acid anhydride, phosgene, the diacidic chlorides or the corresponding anhydrides of fumaric acid, sebacic acid, malonic acid, glutaric acid, adipic acid, succinic acid, tartronic acid, citric acid, malic acid or tartaric acid. Preferred in this regard are the corresponding derivatives of the alkane-carboxylic acids, wherein the alkane radical contains 1 to 3 carbon atoms and possibly has one or two hydroxy groups. Succinic acid is especially preferred.

Examples of suitable glycerolipids having at least one free hydroxy group on the glycerin are monoglycerides, diglycerides and phospholipids. Examples of suitable glycerides are those derived from saturated or unsaturated carboxylic acids having 12 to 14 carbon atoms in the acyl radical, i.e., in which the hydroxy groups on the glycerin which are not free, are esterified with saturated or unsaturated carboxylic acids having 12 to 14 carbon atoms in the alkyl radical, such as, for example, stearic acid, palmitic acid, lauric acid, myristic acid, oleic acid, linoleic acid and linolenic acid and, in the case of phospholipids, one hydroxy group is bonded to phosphoric acid residues known from phosphatidylcholine, phosphatidylethanolamine, phosphatidylserin and other natural phospholipids.

The pharmaceutical vehicle system or prodrug system is applicable to numerous medicaments having one or more hydroxy groups and/or primary or secondary amino groups with a reactive hydrogen atom. Examples of suitable active ingredients of this type are:

(1) Aryl- and heteroaryloxypropanolamine beta blockers such as:
 acebutolol
 alprenolol
 atenolol
 befunolol
 betaxolol
 bevantolol
 bometolol
 bucumolol
 bufetolol
 bufuralol
 bunitrolol
 bunolol
 bupranolol
 carazolol
 carteolol
 celiprolol
 chloropractolol
 cloranolol
 H 87/07
 indenolol
 metipranol
 mepindolol
 metopropol
 moprolol
 medroxalol
 nafetolol
 nifenalol
 nadolol
 oxprenolol
 primidolol
 practolol
 propafenon
 pamatolol
 penbutolol
 pindolol
 propranolol
 talinolol
 tazolol
 timolol
 tolamolol
 trimepranol
(2) Vasodilators
(a) Hydrazinophthalazines and -pyradizines, such as
 hydralazine
 dihydralazine
 ISF 2123
(b) Calcium antagonists with a dihydropyridine carboxylic acid ester structure, such as
 nifedipine
 nimodipine
 nisoldipine
 nicardipine
 niludipine
 ryosidine
 nitrendipine
 SKF 24260
 Hässle H 154/82
(c) other active ingredients (which cannot be chemically classified more nearly) with reactive groups, including reesterifiable carboxylic acid esters (acylates) of pharmacologically active substances, such as
 dopamine
 dobutamine
 methyldopa
 guanethidine
 prazosine
 diltiazem (reesterification)
 prenylamine
 phentolamine
 captopril
 teprotide
 trimazosine
 exiphone
 flecainide
 procainamide
 quinidine
 tocainide
 ajmaline
 prajmaline
 hydroxytriamterene
 furosemide
 spironolactone
 amiloride
 chlortalidone
 xipamide
 benzarone
 benzbromarone
 benziodarone
(d) Thiazide-diuretics, such as
 hydrochlorothiazide
 trichlormethiazide
 cyclopenthiazide
 polythiazide
 butizide
 bemetizide
 hydroflumenthiazide
 ethiazide
 mebutizide
 cyclothiazide
 benzylhydrochlorothiazide
 paraflutizide
 epitizide
 methylclothiazide
 bendroflumethiazide
(3) Aryl- and heteroaryl ethanolamine derivative, including catecholamine, such as
 labetalol
 YM-09, 538
 sulfinanol
 salbutamol
 terbutaline
 fenoterol
 nifenalol
 clenbuterol
 bamethane
 buphenine
 isoxuprin
 zinterol
 norfenefrine
 etilefrine
 octopamine
 synephrine
 phenylephrine
 TA-064
 ephedrine
 orciprenaline
 isoprenaline
 dichloroisoprenaline
 adrenaline
 noradrenaline
(4) Histamine-$H_2$ antagonists
(a) of the cyanoguanidine type, such as
 cimetidine CRC-1970
etindidine
impromidine
oxmetidine
tiotidine
(b) of the ethenediamine type, such as ranitidine
(5) Prostaglandins, prostacyclines, leukotrienes
(6) Cardiac glycosides, such as
digitoxine
digoxine
methyldigoxine
digitoxigenine
gitoxigenine
digoxigenine
methyldigoxine
α- and β-acetyldigoxin
proscillardine
k-strophantine
(7) Diuretics of the thiazide type, such as
chlorothiazide
flumethiazide
hydrochlorothiazide
benzthiazide
trichloromethiazide
cyclopenthiazide
thiabuthiazide
polythiazide
butizide
bemetizide
hydroflumethiazide
(8) Ergot alkaloids, such as
ergotamine
ergosine
methylergometrine
ergocristine
ergocryptine
ergocornine
methysergide
(a) Hydrated ergot alkaloids, such as
dihydroergotamine
dihydroergocornine
dihydroergocristine
dihydroergocryptine
(9) Heparin, heparinoids
(10) Insulin
(11) Chlorambucil
Actinomycin D
4-aminopteroylglutamic acid
Halogen containing x-ray contrast agents with reactive groups
(12) Steroid hormones, such as
testosterone
progesterone
pregnenolone
corticosterone
cortisol
17α-hydroxyprogesterone
cortisone
prednisone
prednisolone
triamphinolone
methylprednisolone
flucortolone
dexamethasone The suitable active ingredients listed hereinabove as examples are designated by their generally known generic names.

Active ingredients thus include:

(a) hydroxy compounds, for example aliphatic alcohols, phenols and enols
(b) compounds of the SH groups, for example mercaptans and thiophenols
(c) compounds with amino groups, for example primary and secondary amines, hydrazines, ureas, guanidines, aminoguanidines, semicarbazides, carbohydrazides, thioureas, thiosemicarbazides, thiocarbohydrazides, and formazanes.

The pharmaceutical vehicle system according to the invention is preferably applicable to the compounds of the afore-cited groups 1, 2a–2c, 3, 5 and 6, in particular groups, 1, 2b and 3, so that A in an especially preferred manner an aryl- or heteroarylethanolamine or an aryl- or heteroaryloxypropanolamine or their hydroxy- or primary or secondary amino group in the ethanolamine or propanolamine part of the molecule reacts with the reactive derivative of the acid yielding the bridge element R.

The process for the preparation of the ultrafine particles in the nanometer range according to the invention comprises (a) dissolving the prodrugs in a water-miscible organic solvent and precipitating them by the addition of water possibly containing a surfactant or an aqueous buffer solution, separating the particles produced in this manner from the liquid phase, washing them and redispersing them in a suitable medium, or (b) dissolving the prodrugs in a volatile solvent, possibly together with a suitable surfactant, evaporating the solvent and dispersing the residue in a suitable dispersant, such as water, a buffer solution or a suitable organic solvent miscible with water or a buffer solution (alcohols, acetone, or the like) by means of vigorous agitation and optionally under the effect of ultrasonic radiation into an ultrafine state, or (c) heating the prodrugs to 5° C. above their melting points, introducing the melt with vigorous agitation drop-by-drop, optionally under ultrasonic radiation, into water optionally containing a surfactant at a water temperature corresponding to the temperature of the melt and cooling the aqueous solution obtained.

In the place of water in the process, a conventional buffer solution may be used in each instance.

Applicable solvents for Stage a) are, for example, dioxane, dimethylsulfoxide (DMSO), tetrahydrofuran, aliphatic alcohols, acetone and other ketones or mixtures of the specified solvents.

Suitable surfactants are, among others, Tweens, Spans, Pluronics, lecithins and, depending on the mode of application, all surface active surfactant classes, such as anionic, cationic and nonionic surfactants.

As the volatile solvents for the process variant (b), for example, chloroform, methylene chloride, toluene, hexane, dichloroethane, may be considered. The surfactants employed are those cited in variant (a) They are also suitable for the variant (c).

Depending on their chemical structure, the prodrugs prepared exhibit a more or less strong surface activity. Whether surfactants should be used at all for the preparation of the ultrafine particles, depends on the chemical structure of the prodrug.

The pharmaceutical vehicle systems produced in this manner may be applied perorally, whereby they are absorbed in the gastrointestinal tract through pinocytosis or other passive adsorption mechanisms. They may also be administered parenterally.

Suitable administration forms are, for example, tablets, capsules, plasters, ultrafine suspensions, implantations, salves, nose drops for systemic effects and the like, which are prepared by conventional methods.

The prodrugs according to the invention are characterized by
high lipophilia
surface activity
good biological compatibility
slow enzymatic dissociation rate, which simultaneously renders possible a depot effect and a reduction of the "first pass" effect, and
multiple galenic processing possibilities.

Thus, they may be prepared, for example, from active ingredients which exhibit poor resorption properties or have a high "first pass" effect following peroral administration. Similarly, active ingredients which are difficult to dissolve, are suitable for the preparation of prodrugs.

The prodrugs according to the invention are new and therefore are also the subject matter of the present invention.

The prodrugs are prepared by the use of processes known in themselves for the production of esters, thioesters, and amides or for the re-esterification of esters beginning with reactive derivatives of the molecular fragments A, R and L, or the molecular fragment compounds themselves, under conventional reaction conditions.

The examples given hereinafter illustrate the invention. Temperatures cited are in Celsius degrees.

EXAMPLE 1

(a) Preparation of the succinic acid monoester of 1,3-dipalmitin 30 g (0.0527 mole) 1, 3-dipalmitylglycerol and 45 g (0.447 mole) succinic acid anhydride are suspended in 750 ml anhydrous benzene and the mixture boiled in the presence of 7.5 ml dry pyridine with reflux and with the exclusion of water. After 25 h, the reaction mixture is cooled, filtered and evaporated to a wax like solid. The product is treated with boiling water and extracted with chloroform after cooling. The chloroform layer is washed with 0.1N HCl and water, dried over MgSO$_4$ and evaporated. The solid product is ground with acetone/heptane/ammonia (25%) (75:25:3) and the precipitate filtered and washed with acetone/heptane (60:40). Following separation, the precipitate is dissolved in chloroform, washed with 0.1N HCl and water, and the chloroform solution dried over MgSO$_4$ and evaporated. After recrystallization from acetone, the above-captioned product is obtained.

(b) Preparation of 1, 3-dipalmityl-succinic acid monoester-acylchloride 30 g (0.045 mole) 1,3-dipalmityl-succinic acid monoester are dissolved with 2 drops of N,N-dimethylformamide in 100 ml dry methylene chloride. The mixture is cooled to 5°, 3 ml thionylchloride added slowly in drops and the entire mixture boiled for 3 h with reflux and the exclusion of water. The solvent is evaporated and the title product recrystallized from n-heptane.

(c) Esterification of Bupranolol-HCl 11.0 g (0.016 mole) 1,3-dipalmitin-succinic acid monoester-acylchloride are dissolved in 350 ml chloroform, cooled to 5° and 1.6 g dry pyridine added. Subsequently, a suspension of 6.2 g bupranolol—HCl in dry chloroform is added in drops over one hour at 5°. The reaction mixture is then further processed for 48 hours under reflux and the exclusion of water at room temperature. The chloroform solution is then washed with 0.1N HCl and water, dried over MgSO$_4$ and evaporated. The rubber-like product obtained in this manner is purified by means of column chromatography. The product may optionally be further processed as in Example 1.

| Elemental analysis | C | H | N |
|---|---|---|---|
| Calculated | 68.99 | 10.05 | 1.52 |
| Determined | 69.02 | 10.15 | 1.53 |

EXAMPLE 2

140 mg of the prodrug prepared according to Example 1 are dissolved with 250 mg Tween 80 in 20 ml chloroform, the chloroform evaporated in a rotary evaporator and 50 ml of a pH 7 phosphate buffer added and the suspension treated with ultrasonic radiation under vigorous agitation for 10 min. Particles of 160 nm (nanometer) are formed.

EXAMPLE 3

140 mg of the prodrug prepared according to Example 1 are melted at 60°, added dropwise to 50 ml of a 0.4% Tween 80 solution in a pH 7 phosphate buffer, which is also heated to 60°, and treated for 10 min under vigorous agitation with ultrasound. The ultrafine emulsion formed is cooled slowly, whereby it is converted into an ultrafine suspension.

EXAMPLE 4

140 mg of the prodrug prepared according to Example 1 are dissolved in a mixture of 7 ml dioxane+30 ml DMSO+100 mg Tween 80. The solution is gradually dripped under vigorous agitation into a 50 ml of a 4% Tween solution in a pH 7 phosphate buffer. The particle size will vary depending on the processing method and the substances used, and their proportions. In most cases, the particle size varies between 0.1–1 $\mu$m.

EXAMPLE 5

200 mg of a pindolol prodrug, prepared according to Example 1 by using a corresponding amount of pindolol—HCl in place of the bupranolol—HCl of Example 1, and 500 mg Tween 80 are dissolved in chloroform, and the chloroform evaporated. The residue is dispersed under the effect of ultrasound in 70.67 ml of a 0.9% NaCl solution, corresponding to 2.83 mg/ml.kg of the pindolol prodrug and 1/mg/ml.kg pindolol. The average particle size is 25 to 50 nm.

EXAMPLE 6

Examples of Application

The following forms were administered i.v or p.o in crossover experiments to four dogs in a randomized series of experiments. Form A: pindolol—HCl, 1 m/ml.kg in a 0.9% NaCl solution. Form B: Preparation according to Example 5. Analysis: 5 ml blood each were taken, heparinized, centrifuged and the plasma stored until the analysis at −20°. Determination was effected for the most part by a fluorometric method specific for nonmodified pindolol in an Ismatec automatic analysis instrument (W. Pacha, Progress in Quality Control in Medicines, Deasy & Zimoney (editors), Elsevier Biomedical Press 1981, Automated Analysis of Pharmakinetic Studies, pp. 155-192). For control, certain of the specimens were reanalyzed by a HPLC method and fluorometric detection (W. Pacha, M. Feltin, to be published).

Results

1. An estimate of the liver first pass effect from $AUC_{iv}$ yields after peroral administration in the case of the product according to the invention a value of only 30%, while it amounts to 70% with the pindolol active ingredient. The assumption that, by means of the prodrug according to the invention, the liver first pass effect may be reduced, is thereby confirmed.

2. Following the intravenous administration of the product according to the invention, an approximately 3 times higher plasma level was found than after the administration of a solution containing unchanged pindolol.

We claim:

1. A pharmaceutical preparation comprising:
   (a) a physiologically compatible carrier substance, and
   (b) a pharmacologically effective amount of ultrafine particles comprised of a compound represented by the formula

A—R—L wherein
   (i) A denotes a residue of a pharmacologically active compound containing at least one group having a reactive hydrogen, said group being selected from a hydroxy group, a mercapto group, and an amino group, said residue being the product of a chemical reaction which comprises reacting said reactive hydrogen;
   (ii) R denotes (1) a residue of an inorganic acid which is at least dibasic or (2) a residue having one to six carbon atoms which is derived from an alkane-carboxylic acid having two or three carboxyl groups; and
   (iii) L denotes a residue of a glycerolipid having a glycerol moiety which is substituted by one or two free hydroxyl groups.

2. A pharmaceutical preparation according to claim 1, wherein said ultrafine particles are comprised of a compound represented by the formula A—(OC—R'—CO—OL)$_n$ wherein
   (i) A denotes a first residue of a pharmacologically active nonheterooxypropanolamine compound comprising at least one reactive hydrogen atom, said first residue being the product of a chemical reaction comprising said reactive hydrogen atom;
   (ii) —OC—R'—CO— denotes a second residue of an alkane-carboxylic acid comprising two or three carboxyl groups, said second residue comprising one to six carbon atoms in alkane moiety R'; and
   (iii) —OL denotes a third residue of a glycerolipid compound, said third residue comprising a glycerol moiety which is substituted by one or two free hydroxyl groups, n being an integer equal to the number of reactive hydrogen atoms in said nonheterooxypropanolamine compound.

3. A pharmaceutical preparation according to claim 1, wherein said carrier substance comprises at least one from the group consisting of an inert galenic carrier and a physiologically compatible solvent.

4. A pharmaceutical preparation according to claim 1, wherein said alkane-carboxylic acid further comprises one or two hydroxyl groups.

5. A pharmaceutical preparation according to claim 2, wherein said alkane moiety R' comprises two carbon atoms.

6. A pharmaceutical preparation according to claim 1, wherein R denotes —SO$_2$—, —PO(OH)—, or —CO—.

7. A pharmaceutical preparation according to claim 2, wherein n is an integer greater than 1.

8. A compound represented by the formula

A—R—L wherein
   (i) A denotes a residue of a pharmacologically active compound containing at least one group having a reactive hydrogen, said group being selected from a hydroxy group, a mercapto group, and an amino group, said residue being the product of a chemical reaction which comprises reacting said reactive hydrogen;
   (ii) R denotes (1) a residue of an inorganic acid which is at least dibasic or (2) a residue having one to six carbon atoms which is derived from an alkane-carboxylic acid having two or three carboxyl groups; and
   (iii) L denotes a residue of a glycerolipid having a glycerol moiety which is substituted by one or two free hydroxyl groups.

9. A compound according to claim 8, said compound being represented by the formula A—(OC—R'—CO—OL)$_n$ wherein
   (i) A denotes a first residue of a pharmacologically active nonheterooxypropanolamine compound comprising at least one reactive hydrogen atom, said first residue being the product of a chemical reaction comprising said reactive hydrogen atom;
   (ii) —OC—R'—CO— denotes a second residue of an alkane-carboxylic acid comprising two or three carboxyl groups, said second residue comprising one to six carbon atoms in alkane moiety R'; and
   (iii) —OL denotes a third residue of a glycerolipid compound, said third residue comprising a glycerol moiety which is substituted by one or two free hydroxyl groups, n being an integer equal to the number of reactive hydrogen atoms in said nonheterooxypropanolamine compound.

10. A compound according to claim 8, wherein said alkane-carboxylic acid further comprises one or two hydroxyl groups.

11. A compound according to claim 9, wherein said alkane moiety R' comprises two carbon atoms.

12. A compound according to claim 8, wherein R denotes —SO$_2$—, —PO(OH)—, or —CO—.

13. A compound according to claim 9, wherein n is an integer greater than 1.

* * * * *